United States Patent
Behl et al.

(10) Patent No.: US 6,451,848 B1
(45) Date of Patent: *Sep. 17, 2002

(54) COMPOSITIONS AND METHODS COMPRISING MORPHINE GLUCONATE

(75) Inventors: Charanjit R. Behl, Hauppauge; Vincent D. Romeo, Massapequa Park; Anthony P. Sileno, Brookhaven, all of NY (US)

(73) Assignee: Nastech Pharmaceutical Company, Inc., Hauppauge, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/626,942

(22) Filed: Oct. 19, 2000

Related U.S. Application Data

(63) Continuation of application No. 09/334,344, filed on Jun. 16, 1999, now Pat. No. 6,225,343.

(51) Int. Cl.⁷ .............. A61K 9/20; A61K 9/22; A61K 31/33; A61K 31/34; A61F 3/00
(52) U.S. Cl. .............. 514/468; 424/434; 424/435; 424/436; 424/464; 424/468; 514/183
(58) Field of Search ................ 424/434, 435, 424/436, 464, 468; 514/183, 468

(56) References Cited

U.S. PATENT DOCUMENTS

| | | | |
|---|---|---|---|
| 4,464,378 A | 8/1984 | Hussain | 424/260 |
| 5,198,209 A | 3/1993 | Zhou et al. | 424/71 |
| 5,202,128 A | 4/1993 | Morella et al. | 424/469 |
| 5,330,766 A | 7/1994 | Morella et al. | 424/490 |
| 5,378,474 A | 1/1995 | Morella et al. | 424/469 |
| 5,508,043 A | 4/1996 | Krishnamurthy | 424/484 |
| 5,629,011 A | 5/1997 | Illum | 424/434 |
| 5,728,695 A | 3/1998 | Harrison et al. | 514/230.8 |
| 5,730,997 A | 3/1998 | Lienhop et al. | 424/439 |
| 5,756,483 A | 5/1998 | Merkus et al. | 514/58 |
| 5,830,892 A | 11/1998 | Baker | 514/236.2 |
| 5,877,316 A | 3/1999 | Haworth et al. | 544/138 |
| 5,880,132 A | 3/1999 | Hill | 514/282 |
| 5,885,999 A | 3/1999 | Elliott | 514/258 |
| 5,942,251 A | 8/1999 | Merkus | 424/493 |

FOREIGN PATENT DOCUMENTS

| WO | 82/03768 | 11/1982 | 31/40 |
|---|---|---|---|

OTHER PUBLICATIONS

Banker and Rhodes, eds., *Modern Pharmaceutics*, Chapter 2, pp. 23–74, Marcel Dekker Inc., New York, 1979.

Primary Examiner—Thurman K. Page
Assistant Examiner—S. Tran
(74) Attorney, Agent, or Firm—Woodcock Washburn LLP

(57) ABSTRACT

The present invention relates to a pharmaceutical composition which includes morphine gluconate or chemical equivalent thereof. In one embodiment, the present invention includes a method of making morphine gluconate or chemical equivalent thereof by mixing morphine sulfate with sodium gluconate. The present invention also includes a method for eliciting an analgesic or anesthetic response in a mammal which includes administering a therapeutically effective amount of a pharmaceutical composition including morphine gluconate or chemical equivalent thereof.

21 Claims, 7 Drawing Sheets

FIG. 4  PLOTS OF AVERAGE FREE MORPHINE PLASMA CONC. vs. TIME FOR MORPHINE SULFATE NASAL SPRAY

COMPOSITIONS AND METHODS COMPRISING MORPHINE GLUCONATE

This application is a continuation of applicational Ser. No. 09/334,344 filed Jun. 16, 1999 now U.S. Pat. No. 6,225,343.

FIELD OF THE INVENTION

The present invention relates to compositions and methods comprising morphine gluconate for eliciting an analgesic or anesthetic response in a mammal.

BACKGROUND OF THE INVENTION

The compound morphine or (−)7,8-didehydro-4,5α-epoxy-17-methylmorphinan-3,6α-diol, is a phenanthrene derivative that exhibits the following general structure:

Structure A (see page before claims)

Morphine is a centrally acting narcotic analgesic that acts as an agonist primarily at mu, kappa and perhaps delta receptors in the central nervous system. By acting on these receptors, morphine causes analgesia and anesthesia as a result of a receptor-mediated central action on pain perception, together with a receptor-medicated modulatory effect on the central transmission of noxious sensation. Some side effects caused by morphine include drowsiness, respiratory depression and euphoria.

Various morphine compositions are known in the pharmaceutical arts. For example, morphine sulfate is one of the most commonly prescribed morphine compositions. Other morphine compositions such as morphine tartrate and morphine lactate are disclosed in U.S. Pat. No. 5,880,132 issued to Hill and U.S. Pat. No. 5,378,474 to Morella et al. for the treatment and prevention of pain or nociception. Some polar compositions of morphine including morphine-3-glucuronide and morphine-6-glucuronide are disclosed in U.S. Pat. No. 5,629,011 to Illum. While these references discuss different pharmaceutical compositions of morphine, none disclose morphine gluconate or a chemically modified equivalents thereof.

Morphine has been used for a variety of clinical indications. Some examples of such indications include analgesia, for treatment of acute and chronic pain, anesthesia during surgery and to allay anxiety during acute pulmonary edema.

Several delivery routes have been utilized for administering morphine. These routes include oral, injectable, buccal and intranasal administration. For example, oral and injectable morphine sulfate are commonly prescribed for cancer pain. Oral and injectable morphine sulfate are available from Abbott Pharmaceuticals Inc., USA.

Other more desirable delivery routes have been investigated. For example, intranasal delivery of morphine has shown potential for rapid onset and duration of action. Further, intranasal administration offers minimal delays in absorption, is not as invasive as intravenous delivery and achieves therapeutically effective amounts of the drug in plasma. For example, intranasal delivery of morphine is disclosed in U.S. Pat. No. 5,629,011 to Illum and U.S. Pat. No. 4,464,378 to Hussain for the treatment of chronic and acute pain. The entire disclosure of U.S. Pat. No. 5,629,011 and U.S. Pat. No. 4,464,378 is herein incorporated by reference. While these references discuss the benefits of intranasal delivery of morphine, there is no consideration of using morphine gluconate or chemical equivalent thereof as an analgesic or anesthetic.

Based on the foregoing, there is a need for effective morphine compositions and methods for eliciting analgesic and anesthetic responses. The morphine compositions and methods of the present invention include morphine gluconate or chemical equivalent thereof.

SUMMARY OF THE INVENTION

The present invention provides a pharmaceutical composition which includes morphine gluconate or chemical equivalent thereof.

In one embodiment, the present invention provides a pharmaceutical composition which includes a therapeutically effective amount of morphine gluconate or chemical equivalent thereof for eliciting an analgesic or anesthetic response in a mammal.

It another embodiment, the present invention provides a method of making a pharmaceutical composition which includes morphine gluconate or chemical equivalent thereof by mixing morphine sulfate with sodium gluconate to yield morphine gluconate or chemical equivalent thereof.

In yet another embodiment, the present invention provides a method for eliciting an analgesic or anesthetic response in a mammal which includes administering a therapeutically effective amount of a pharmaceutical composition which includes morphine gluconate or chemical equivalent thereof to the mammal that is sufficient to elicit analgesia or anesthesia.

In still yet another embodiment, the present invention provides a pharmaceutical composition which includes morphine gluconate or chemical equivalent thereof, prepared by mixing morphine sulfate with sodium gluconate to yield morphine gluconate or chemical equivalent thereof.

The present invention also relates to a method for eliciting an analgesic or anesthetic response in a mammal comprising nasally administering a therapeutically effective amount of a pharmaceutical composition which includes morphine gluconate or chemical equivalent thereof to the mammal in combination with a nasal delivery system.

DETAILED DESCRIPTION OF THE PREFERRED EMBODIMENTS

Figure 1:
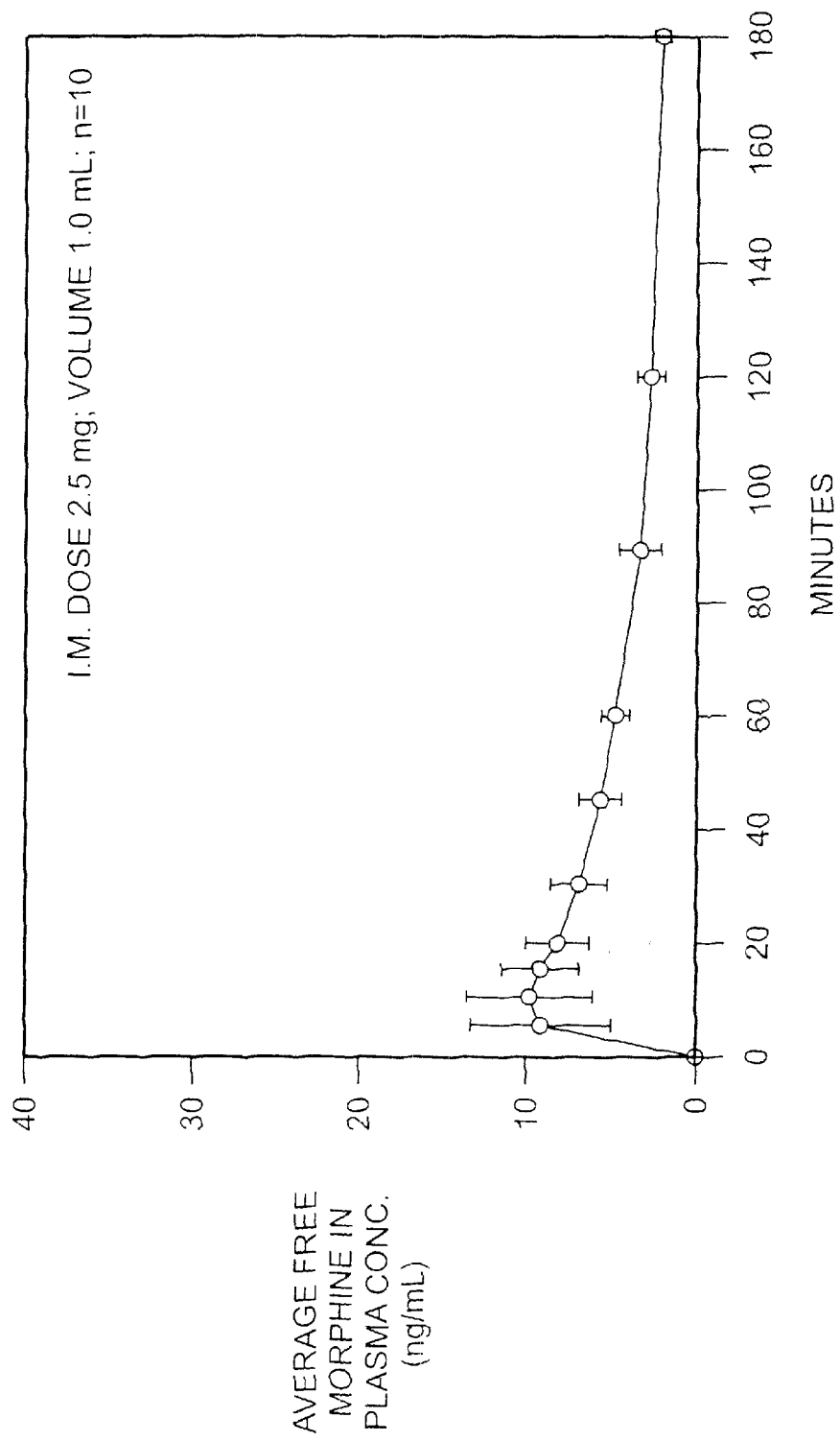
FIG. 1 is a graph showing plasma concentrations of free morphine achieved upon administering 2.5 mg of morphine sulfate by intramuscular injection.

The present invention is a pharmaceutical composition which includes morphine gluconate or chemical equivalent thereof. As used herein, pharmaceutical compositions include any pharmaceutically acceptable carrier which incorporates the active agent, i.e., morphine gluconate or chemical equivalents thereof.

Morphine gluconate exhibits the following general structure:

Structure B (see page before claims)

For purposes of the present invention, chemical equivalents of morphine gluconate include all anionic, cationic and non-ionic reaction complexes between the morphine molecule or (-)7,8-didehydro-4,5α-epoxy-17-methylmorphinan-3,6α-diol and the gluconate moiety. Such complexes typically react with the hydroxyl group of the morphine molecule at the C3 or C6 positions. The gluconate moiety includes D-gluconic acid, gluconic acid, glycogenic acid, glycan-_-lactone, and the like. The chemical equivalents of morphine gluconate function in a similar manner in the body, such as for example prodrugs, analogs, biologically active fragments and the like. As used herein, morphine gluconate also includes compositions comprising morphine sulfate and sodium gluconate.

The present invention includes a method of making morphine gluconate or chemical equivalent thereof which includes mixing morphine with a gluconate moiety to yield morphine gluconate. Preferably, the gluconate moiety is a pharmaceutically acceptable gluconate salt. Such salts include calcium gluconate, potassium gluconate, magnesium gluconate, lithium gluconate, sodium gluconate and the like.

Morphine gluconate or chemical equivalent thereof may be prepared using starting reactants that are readily available. For example, morphine sulfate is available from Abbott Pharmaceuticals Inc., USA, and sodium gluconate is available from Spectrum Inc., USA. In one preferred embodiment, morphine gluconate is prepared by mixing morphine sulfate with sodium gluconate to yield morphine gluconate or chemical equivalent thereof.

It will be understood by those skilled in the art that other morphine salts and gluconate salts can be used to yield morphine gluconate or chemical equivalent thereof. Some examples of gluconate salts include salts of alkali metals and alkaline earth metals such as magnesium gluconate, potassium gluconate, lithium gluconate and the like. Morphine salts include salts of mineral acids such as hydrochloric, hidrotic, hydrobromic, phosphoric, metaphosphoric, and nitric acids, as well as salts of organic acids such as tartaric, acetic, citric, malic, benzoic, and lactic acid. For example, morphine tartrate, morphine lactate, or morphine hydrochloride can be reacted with the gluconate moiety to yield morphine gluconate or chemical equivalent thereof.

The amount of morphine salt, such as for example, morphine sulfate and gluconate salt, such as for example, sodium gluconate that can be used to make morphine gluconate or chemical equivalent thereof can vary depending on the amount of reactants used. Preferably, the amount of morphine salt used is from about 0.01% to about 40%, more preferably, from about 1% to about 10%, and most preferably, from about 3% to about 5% by weight of the total weight of the composition (w/w). Preferably, the amount of gluconate salt used is from about 0.01% to about 50%, more preferably, from about 5% to about 20%, and most preferably, from about 5% to about 15% (w/w). In any event, the practitioner is guided by skill and knowledge in the field, and the present invention includes without limitation amounts of reactants which are effective to achieve the desired yields.

In the most preferred embodiment, morphine sulfate and sodium gluconate are dissolved in a suitable solvent to yield morphine gluconate or chemical equivalent thereof. Suitable solvents include water, alcohol, glycerin, propylene glycol, and the like. Preferably, the amount of solvent is sufficient to dissolve the morphine and gluconate salts. Most preferably, water is mixed with morphine sulfate and sodium gluconate to yield morphine gluconate or chemical equivalent. Preferably, the reaction is carried out at room temperature and at one atmosphere of pressure.

In an alternate embodiment, the present invention provides a pharmaceutical composition which includes morphine gluconate or chemical equivalent thereof, prepared by mixing morphine sulfate with sodium gluconate to yield morphine gluconate or chemical equivalent thereof. As stated above, most preferably, morphine sulfate and sodium gluconate are dissolved in a suitable solvent to yield morphine gluconate or chemical equivalent thereof.

Therapeutically Effective Amounts

As used herein, a therapeutically effective amount is that amount effective to elicit an analgesic or anesthetic response. For example, morphine gluconate or chemical equivalent thereof can achieve the relief or palliation of acute or chronic pain. Preferably, morphine gluconate is administered in an amount that limits the most common side effects such as respiratory depression, constipation and lethargy.

The minimal dosage of morphine gluconate is the lowest dosage which elicits analgesia or anesthesia in the mammal. For example, morphine gluconate or chemical equivalent thereof can be administered at a minimal dosage of preferably from at least about 0.01 mg/kg to about 4 mg/kg of body weight, more preferably from at least about 1 mg/kg to about 4 mg/kg of body weight, and most preferably from at least about 2 mg/kg to about 4 mg/kg of body weight.

Maximal dosage for a mammal is the highest dosage which elicits analgesia or anesthesia which does not cause undesirable or intolerable side effects such as respiratory depression. In any event, the practitioner is guided by skill and knowledge in the field, and the present invention includes without limitation dosages which are effective to achieve the described effect in the mammal.

As used herein, analgesia or an analgesic response includes relieving pain in the mammal without causing loss of consciousness. Typically, morphine gluconate or chemical equivalents thereof can be used to elicit analgesia in the treatment of acute and chronic pain. Morphine gluconate or chemical equivalents thereof can also be used to produce anesthesia or an anesthetic response in the mammal. Typically, the mammal experiences loss of feeling or sensation, especially loss in pain sensation, to permit the performance of surgery or other painful procedures. Accordingly, when analgesia is induced the mammal loses consciousness.

Mammals include, for example, humans, as well as pet animals such as dogs and cats, laboratory animals, such as rats and mice, and farm animals, such as horses and cows.

Administration

Morphine gluconate or chemical equivalent thereof can be administered orally, parenterally, intranasally, vaginally, rectally, lingually, sublingually, bucally, intrabuccaly and transdermally to the mammal.

Accordingly, morphine compositions designed for oral, lingual, sublingual, buccal and intrabuccal administration can be made, with an inert diluent or with an edible carrier. Morphine compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various composition, should be pharmaceutically pure and non-toxic in the amounts used.

Morphine compositions of the present invention can easily be administered parenterally such as for example, by intravenous, intramuscular, intrathecal or subcutaneous injection. Parenteral administration can be accomplished by incorporating the morphine compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving morphine gluconate in the glycerin, mixing the heated glycerin after which purified water may be added, and pouring the hot mixture into a suppository mold.

Transdermal administration includes percutaneous absorption of morphine gluconate through the skin, which results in systemic effects such as analgesia or anesthesia. Transdermal formulations include patches, ointments, creams, gels, salves and the like.

The present invention includes nasally administering to the mammal a therapeutically effective amount of morphine gluconate or chemical equivalent thereof. As used herein, nasally administering or nasal administration includes administering morphine gluconate or chemical equivalent thereof to the mucous membranes of the nasal passage or nasal cavity of the mammal.

In one embodiment, the present invention provides a pharmaceutical composition comprising a therapeutically effective amount of morphine gluconate or chemical equivalent thereof in combination with a nasal delivery system.

As used herein, pharmaceutical compositions include therapeutically effective amounts of morphine gluconate or chemical equivalent thereof as discussed above. Such compositions can be administered, for example, as a nasal spray, nasal drop, suspension, gel, ointment, cream or powder. Administration of morphine compositions of the present invention may also take place using a nasal tampon or nasal sponge containing morphine gluconate.

Nasal powder compositions can be made by mixing morphine gluconate or chemical equivalent thereof with an excipient, both possessing the desired particle size. Other methods to make a suitable powder formulation can be selected. First, a solution of morphine gluconate is made, followed by precipitation, filtration and pulverization. It is also possible to remove the solvent by freeze drying, followed by pulverization of the powder in the desired particle size by using conventional techniques, known in the pharmaceutical arts. The final step is size classification for instance by sieving, to get the desired particle size. Powders can be administered using a nasal insufflator other suitable device.

Powders may also be administered in such a manner that they are placed in a capsule. The capsule is set in an inhalation or insufflation device. A needle is penetrated through the capsule to make pores at the top and the bottom of the capsule and air is sent to blow out the powder particles. Powder formulation can also be administered in a jet-spray of an inert gas or suspended in liquid organic fluids.

Morphine gluconate or chemical equivalent thereof can also be brought into a viscous base, using systems, conventionally used, for example natural gums, methylcellulose and derivatives, acrylic polymers (carbopol) and vinyl polymers (polyvinylpyrrolidone). Pharmaceutical compositions of the present invention may include, many other excipients, known from the pharmaceutical arts, such as preservatives, surfactants, co-solvents, adhesives, antioxidants, buffers, viscosity enhancing agents and agents to adjust the pH and osmolarity.

Preferably, morphine gluconate or chemical equivalent thereof is combined with a suitable delivery system for absorption across the nasal mucosa of a mammal. The nasal delivery system includes a pharmaceutically acceptable buffer, a thickening agent, a humectant, surfactant and combinations thereof. Such nasal delivery system can take various forms including for example, aqueous solutions and non-aqueous solutions.

Aqueous solutions, include for example, aqueous gels, aqueous suspensions, aqueous liposomes, aqueous emulsions, aqueous microemulsions. Non aqueous solutions include, for example, non-aqueous gels, non-aqueous suspensions, non-aqueous liposomes, non-aqueous emulsions and non-aqueous microemulsions.

The present delivery systems also include all types of particulate formulations, including for example, simple powder mixtures as set forth above, powder microspheres (coated and uncoated), ribosomes and mixtures thereof.

The various forms of the delivery system set forth above can include a buffer to maintain the pH of morphine gluconate or chemical equivalent thereof, a pharmaceutically acceptable thickening agent, humectant and surfactant.

With respect to the non-aqueous and powder formulations set forth above, suitable forms of buffering agents can be selected so that when the formulation is delivered into the nasal cavity of a mammal, selected pH ranges are achieved therein upon contact with, e.g., the nasal mucosa.

In the present invention, the pH of morphine gluconate compositions should be maintained below about 10. Compositions having a pH of less than about 3 or greater than about 10 can increase the risk of irritating the nasal mucosa of a recipient. Most preferably, the pH is below about 9, such pH is well tolerated by the mammal.

The morphine gluconate compositions of the present invention may include a pH adjusting agent, such as for example, trolamine. Preferably, trolamine is added to the composition as needed to maintain the pH below about 9.

The viscosity of the compositions of the present invention can be maintained at a desired level using a pharmaceutically acceptable thickening agent. Thickening agents that can be used in accordance with the present invention include for example, methyl cellulose, xanthan gum, carboxymethyl cellulose, hydroxypropyl cellulose, carbomer, polyvinyl alcohol, alginates, acacia, chitosans and combinations thereof. The concentration of the thickening agent will depend upon the agent selected and the viscosity desired. Such agents will also be used in the particulate formulations of the present invention.

The compositions of the present invention may also include a tolerance enhancer to reduce or prevent drying of the mucus membrane and to prevent irritation thereof. Suitable tolerance enhancers that can be used in the present invention include humectants, such as for example, sorbitol, propylene glycol, mineral oil, vegetable oil, glycerol, glycerin, soothing agents, membrane conditioners, sweeteners and combinations thereof. The concentration of the tolerance enhancer(s) in the present compositions will also vary with the agent selected. The tolerance enhancer can be present in the delivery system in a concentration ranging from about 0.01% to about 20% by weight of the pharmaceutical composition.

In order to enhance absorption of the morphine gluconate or chemical equivalent thereof through the nasal mucosa, a therapeutically acceptable surfactant or absorption enhancer can be added to the nasal delivery system. Such surfactant or absorption enhancer increases plasma levels of free morphine above that observed without the absorption enhancer or surfactant. Preferably, free morphine plasma concentrations are increased by from about 10% to about 100%. Accordingly, a lower amount of drug can be used to achieve the same therapeutic levels.

Suitable surfactants or absorption enhancers that can be used in accordance with the present invention include, for example, oleic acid, polyoxyethylene derivatives of fatty acids, partial esters of sorbitol anhydride, such as for example, tween 80, tween 20, polyoxyl 40 stearate, polyoxy ethylene 50 stearate, fusieates, bile salts, octoxynol and combinations thereof. Suitable surfactants include nonionic, anionic and cationic surfactants. These surfactants can be present in the delivery system in a concentration ranging from about 0.001% to about 20% by weight. A most preferred formulation of morphine gluconate or chemical equivalent thereof includes from about 0.01% to about 20% by weight of tween 20 and from about 0.01% to about 50% by weight of oleic acid to enhance nasal absorption.

In the present invention other optional ingredients may also be incorporated into the nasal delivery system provided they do not interfere with the action of morphine gluconate or significantly decrease the absorption of it across the nasal mucosa. Such ingredients can include, for example, pharmaceutically acceptable excipients and preservatives. The excipients that can be used in accordance with the present invention include, for example, bio-adhesives and/or swelling/thickening agents and combinations thereof.

To extend shelf life, preservatives can be added to the present compositions. Suitable preservatives that can be used with the present compositions include, for example, benzyl alcohol, parabens, thimerosal, chlorobutanol, benzalkonium and combinations thereof, with benzalkonium chloride being preferred. Typically, the preservative will be present in the compositions in a concentration of from about 0.001% up to about 1% by weight of the total composition. The exact concentration of the preservative, however, will vary depending upon the intended use and can be easily ascertained by one skilled in the art.

Other ingredients which extend shelf life can be added such as for example, antioxidants. Some examples of antioxidants include sodium metabisulfite, potassium metabisulfite, ascorbyl palmitate and the like. Typically, the antioxidant will be present in the compositions in a concentration of from about 0.001% up to about 5% by weight of the total composition.

It has been unexpectedly discovered that pharmaceutical compositions comprising morphine gluconate or chemical equivalent, achieve adequate plasma levels. Accordingly, morphine gluconate or chemical equivalent thereof, can be used to achieve analgesic or anesthetic effects as that observed with morphine sulfate.

The following examples are set forth to illustrate the formulations of the present invention, as well as the surprising results achieved therewith. These examples are provided for purposes of illustration only and are not intended to be limiting in any sense.

EXAMPLE 1

Intramuscular (i.m.) Administration of Morphine Sulfate

Figure 2:
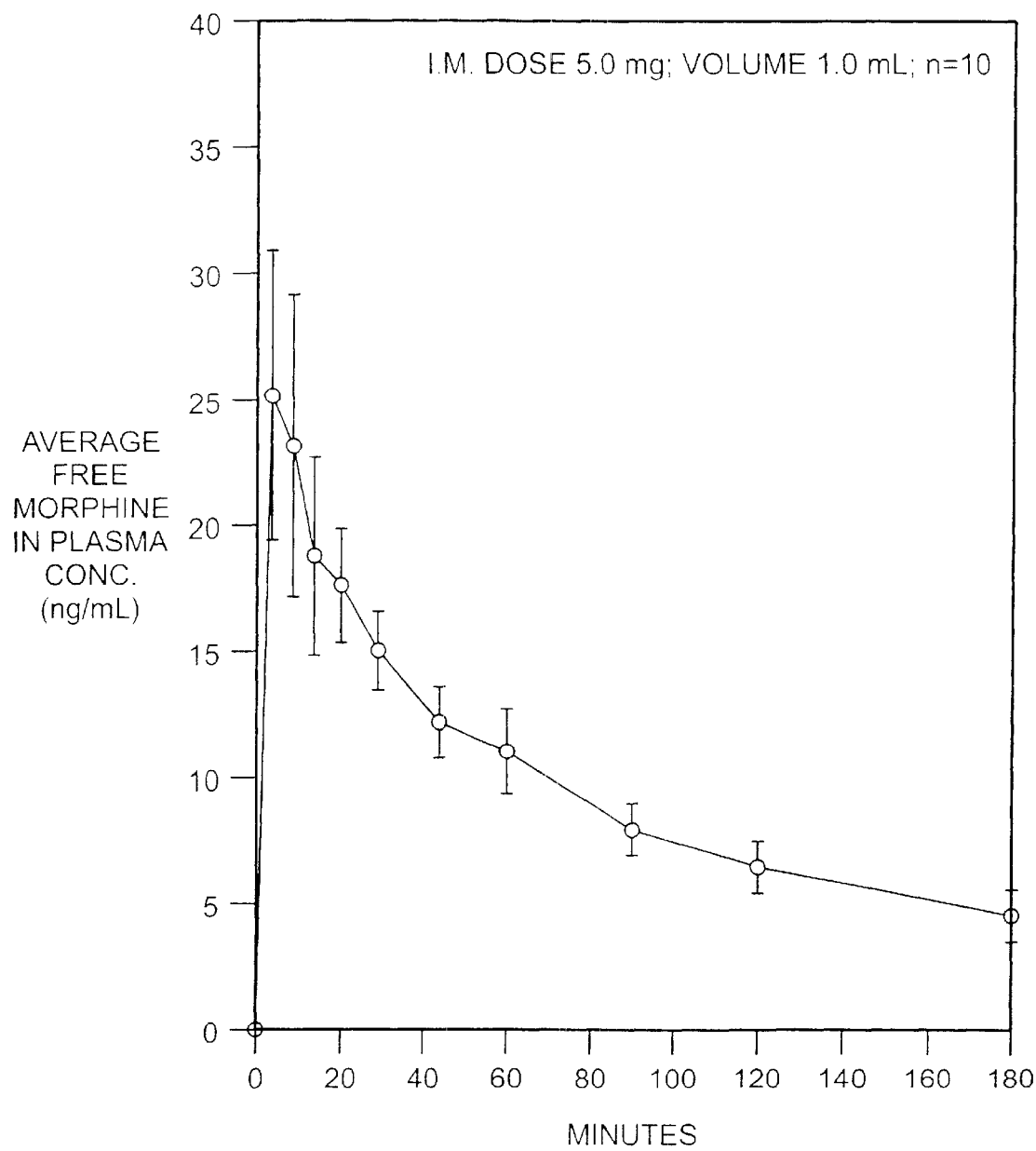
FIG. 2 is a graph showing plasma concentrations of free morphine achieved upon administering 5 mg of morphine sulfate by intramuscular injection.

Morphine sulfate was administered intramuscularly to healthy volunteers. FIGS. 1 and 2 show the plasma concentrations of free morphine achieved after 2.5 mg and 5 mg of morphine sulfate was administered intramuscularly. The average peak concentrations ($C_{MAX}$) and time in minutes for the average peak concentration ($T_{MAX}$) are shown in Table 1. It was observed that 2.5 mg of morphine sulfate i.m. achieved average peak plasma concentrations of approximately 10.7 ng/ml within approximately 10 minutes after administration. Morphine sulfate 5 mg i.m. achieved average peak plasma concentrations of approximately 10.7 ng/ml within approximately 8 minutes after administration.

EXAMPLE 2

Intranasal Administration of Morphine Gluconate

Morphine gluconate was administered intranasally to healthy human volunteers. The formulation was prepared as described below:

| Formulation 3 | |
|---|---|
| Composition | Quantity - 100 Gm (% w/w) |
| Morphine Sulfate, USP | 3.2 |
| Sodium Gluconate, USP | 12.0–15.0 |
| Trolamine, NF | to adjust pH |
| Purified Water, USP | 100 q.s. |

Figure 3:
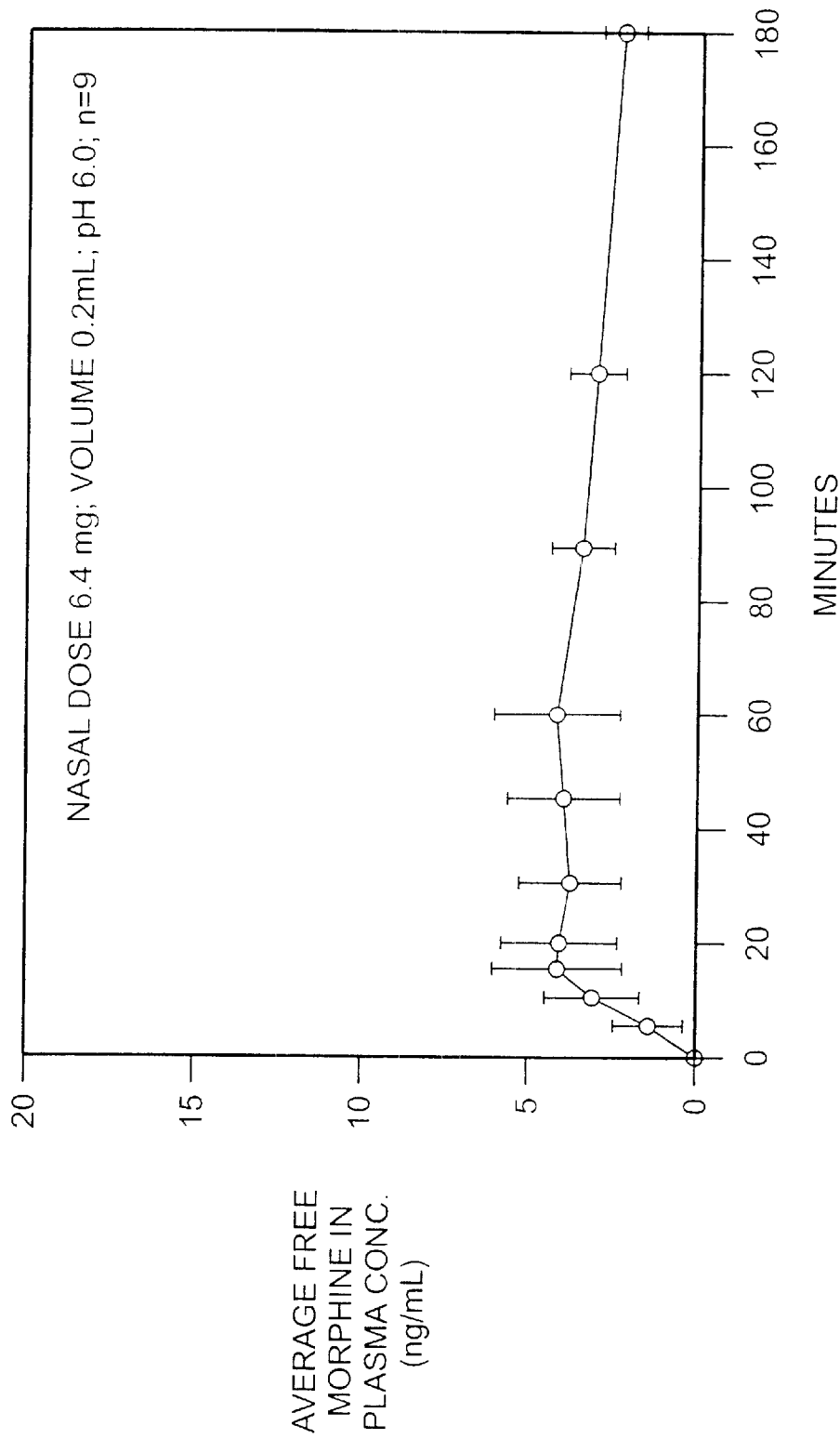
FIG. 3 is a graph showing plasma concentrations of free morphine achieved upon administering 6.4 mg of morphine gluconate intranasally.
Figure 4:
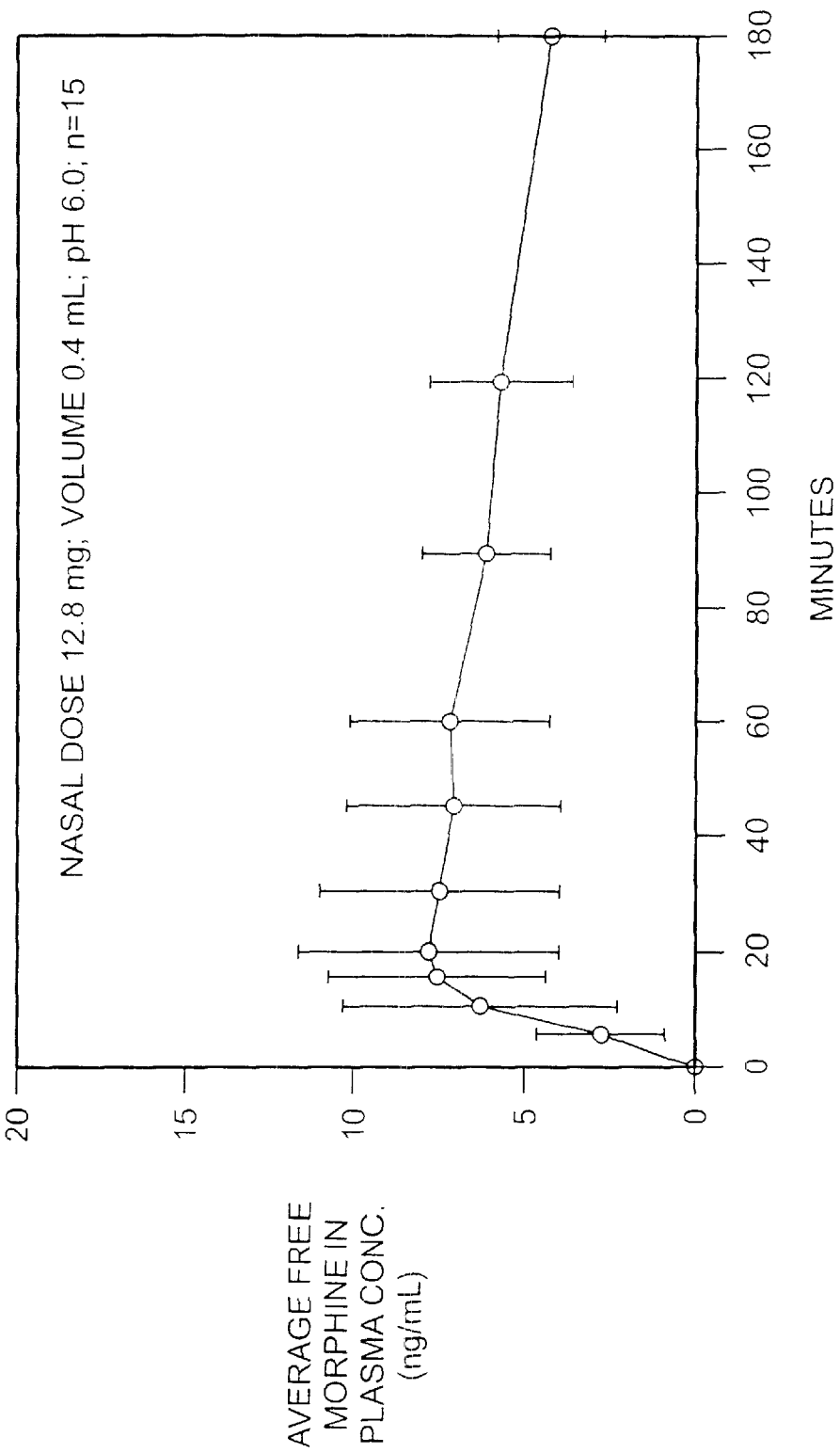
FIG. 4 is a graph showing plasma concentrations of free morphine achieved upon administering 12.8 mg of morphine gluconate intranasally.

FIGS. 3 and 4 show the plasma concentration of free morphine achieved after 6.4 mg and 12.8 mg of morphine gluconate were administered intranasally using Formulation 3. The average peak concentrations ($C_{MAX}$) and time in minutes for the average peak concentration ($T_{MAX}$) are shown in Table 1. It was observed that 6.4 mg of morphine gluconate achieved average peak plasma concentrations of approximately 5.9 ng/ml within approximately 38 minutes after administration. Also, 12.8 mg of morphine gluconate achieved average peak plasma concentrations of approximately 9.5 ng/ml within approximately 51 minutes after administration.

EXAMPLE 3

Intranasal Administration of Morphine Gluconate

Morphine gluconate was administered intranasally to healthy human volunteers. This formulation included oleic acid as an absorption enhancer. The formulation was prepared as described below:

Formulation 4

| Composition | Quantity - 100 Gm (% w/w) |
| --- | --- |
| Morphine Sulfate, USP | 3.2 |
| Sodium Gluconate, USP | 15.0 |
| Glycerine, USP | 5.0 |
| Tween 20, NF | 5.0 |
| Oleic Acid, NF | 0.25 |
| Trolamine, NF | to adjust pH |
| Purified Water, USP | 100 q.s. |

Figure 5:
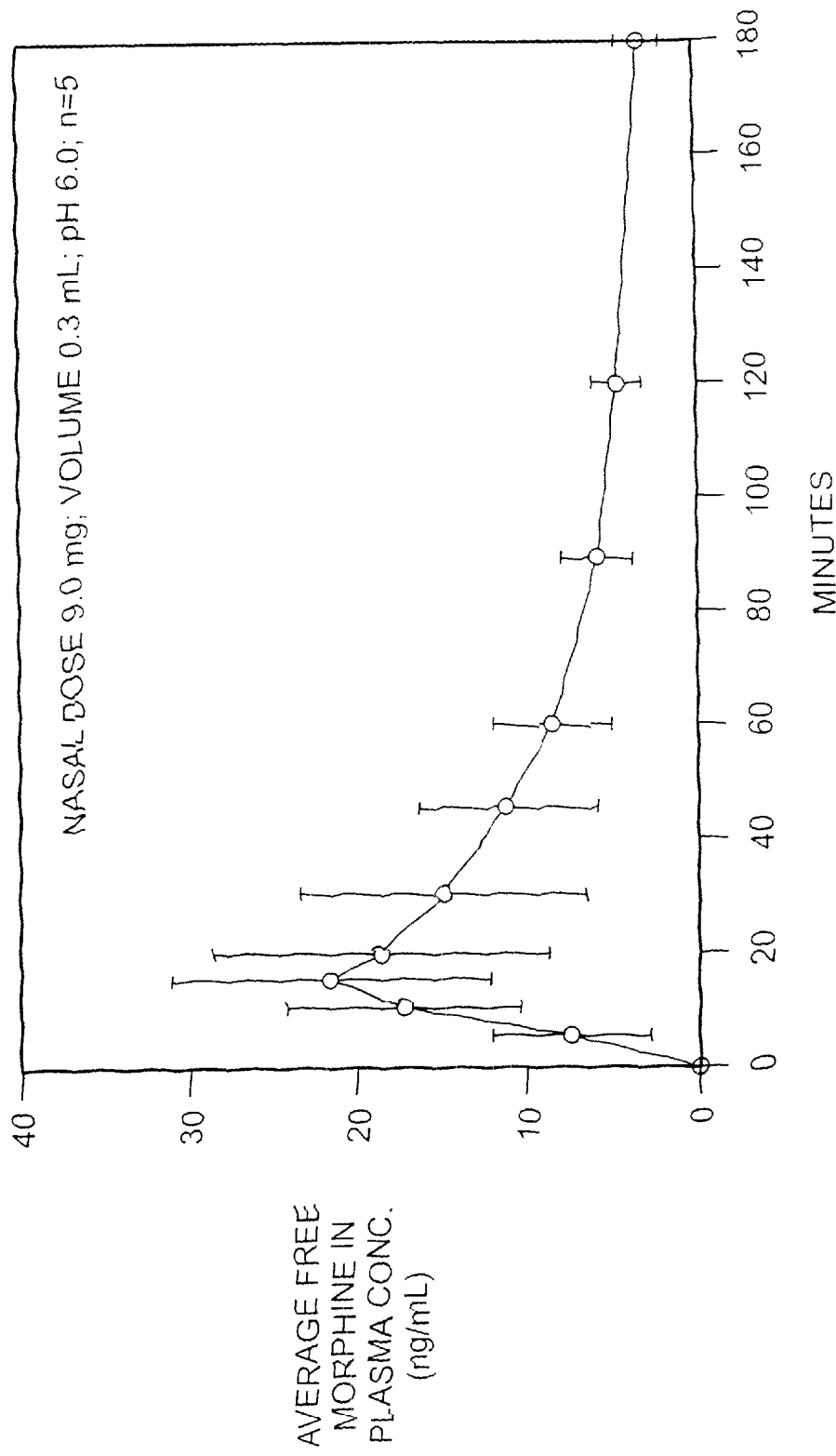
FIG. 5 is a graph showing plasma concentrations of free morphine achieved upon administering 9 mg of morphine gluconate intranasally.
Figure 6:
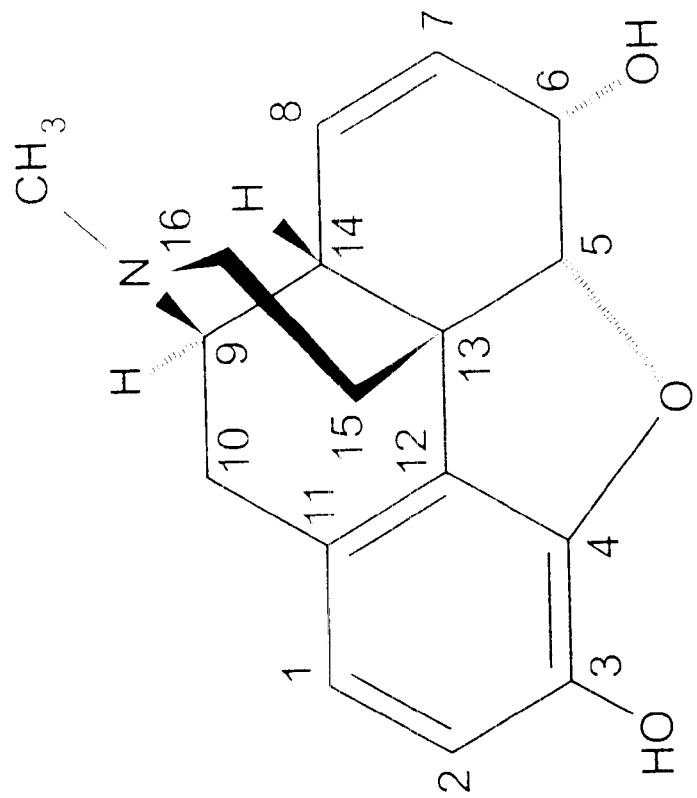
Figure 7:
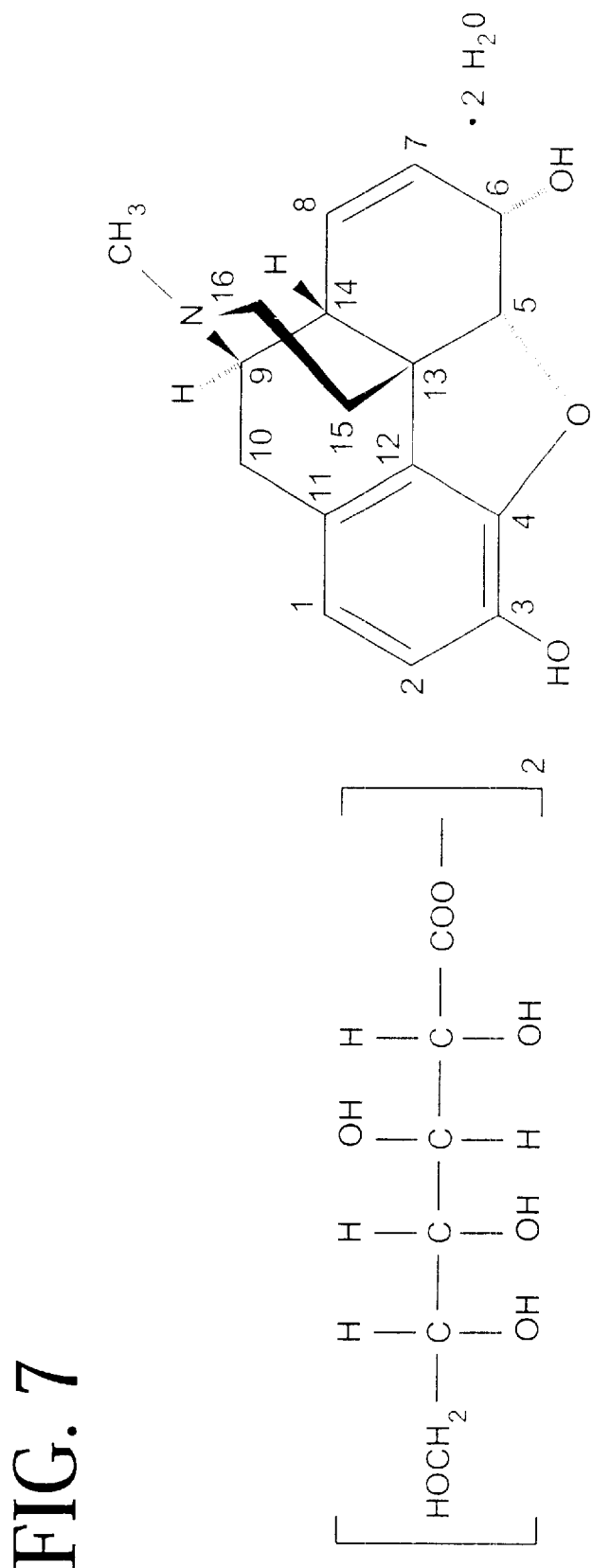

FIG. 5 shows the plasma concentration of free morphine achieved after 9 mg of morphine gluconate was administered intranasally using Formulation 5. The average peak concentration ($C_{MAX}$) and time in minutes for the average peak concentration ($T_{MAX}$) are shown in Table 1. It was observed that 9 mg of morphine gluconate achieved average peak plasma concentrations of approximately 21.6 ng/ml within approximately 5 minutes after administration.

Comparing these results to FIGS. 1–4, this example shows that morphine gluconate when intranasally administered is rapidly absorbed. Morphine gluconate achieves peak plasma concentrations equivalent to the sulfate salt of morphine, when morphine sulfate is administered intramuscularly. Also, the use of an absorption enhancer, such as oleic acid, provided increased onset and peak plasma concentrations of free morphine as compared to morphine gluconate formulations without oleic acid. This pharmacokinetic profile is useful for eliciting analgesia.

TABLE 1

| Formulation No. | Formulation | Average $C_{MAX}$ (ng/ml) | Average $T_{MAX}$ (minutes) |
| --- | --- | --- | --- |
| 1 | Morphine Sulfate 2.5 mg I.M. (n = 10) | 10.7 | 10 |
| 2 | Morphine Sulfate 5 mg I.M. (n = 10) | 26.4 | 8 |
| 3 | Morphine gluconate 6.4 mg nasal, pH 6.0 (n = 10)* | 5.9 | 38 |
| 3 | Morphine gluconate 12.8 mg nasal, pH 6.0. (n = 15)* | 9.5 | 51 |
| 4 | Morphine gluconate 9 mg nasal, pH 6.0 (n = 5)* | 21.6 | 5 |

*The intranasal formulations were well tolerated by the volunteers and produced analgesia. No significant adverse effects were noted.

The invention being thus described, it will be obvious that the same may be varied in many ways. Such variations are not to be regarded as a departure from the spirit and scope of the invention and all such modifications are intended to be included within the scope of the following claims.

What is claimed is:

1. A pharmaceutical composition comprising morphine sulfate and sodium gluconate or chemical equivalent thereof effective in said composition to elicit an analgesic or anesthetic response in a mammalian subject.

2. A method of making a pharmaceutical composition comprising morphine gluconate or chemical equivalent thereof effective to elicit an analgesic or anesthetic response in a mammalian subject comprising mixing morphine sulfate with sodium gluconate to yield morphine gluconate or chemical equivalent thereof.

3. A method according to claim 2, further comprising dissolving morphine sulfate and sodium gluconate in a suitable solvent to yield morphine gluconate or chemical equivalent thereof.

4. A pharmaceutical composition comprising morphine gluconate or chemical equivalent thereof effective to elicit an analgesic or anesthetic response in a mammalian subject, prepared by mixing morphine sulfate with sodium gluconate to yield morphine gluconate or chemical equivalent thereof.

5. A pharmaceutical composition prepared according to claim 4, wherein morphine sulfate and sodium gluconate are dissolved in a suitable solvent to yield morphine gluconate or chemical equivalent thereof.

6. A method of eliciting an analgesic or anesthetic response in a mammal comprising administering a therapeutically effective amount of morphine gluconate or chemical equivalent thereof effective to elicit an analgesic or anesthetic response in said mammal to the mammal which is sufficient to elicit analgesia or anesthesia.

7. A method according to claim 6, wherein the morphine gluconate or chemical equivalent thereof is administered orally, parenterally, intranasally, vaginally, rectally, lingually, sublingually, bucally, intrabuccaly and transdermally to the mammal.

8. A method for eliciting an analgesic or anesthetic response in a mammal comprising nasally administering a therapeutically effective amount of morphine gluconate or chemical equivalent thereof effective to elicit an analgesic or anesthetic response in said mammal to the mammal in combination with a nasal delivery system.

9. A method according to claim 8, wherein the morphine gluconate or chemical equivalent thereof is dispersed in an aqueous or non-aqueous formulation.

10. A method according to claim 8, wherein the aqueous formulation is at a pH below about 9.0.

11. A method according to claim 8, wherein morphine gluconate is at a concentration below about 50% w/w.

12. A method according to claim 7, wherein morphine gluconate is dispersed in suspensions, powders, gels, ointments and creams.

13. A method according to claim 8, wherein the nasal delivery system comprises a buffer to maintain the pH of morphine gluconate or chemical equivalent thereof, a pharmaceutically acceptable thickening agent, a humectant, a pharmaceutically acceptable surfactant and combinations thereof.

14. A method according to claim 13 further comprising one or more pharmaceutical excipients.

15. A method according to claim 13 further comprising a pharmaceutically acceptable preservative.

16. A method according to claim 13, wherein the buffer is selected from the group consisting of acetate, citrate, prolamine, carbonate and phosphate and combinations thereof.

17. A method according to claim 13, wherein the thickening agent is selected from the group consisting of methyl cellulose, xanthan gum, carboxymethyl cellulose, hydroxypropyl cellulose, carbomer, polyvinyl alcohol, alginates, acacia, chitosan and combinations thereof.

18. A method according to claim 13, wherein the humectant is selected from the group consisting of sorbitol, propylene glycol, glycerol, mineral oil, vegetable oil and combinations thereof.

19. A method according to claim 13, wherein the surfactant is selected from the group consisting of polyoxyethylene derivatives and fatty acid partial esters of sorbitol anhydrides, oleic acid and combinations thereof.

20. A method according to claim 13, wherein the surfactant is selected from the group consisting of sodium lauryl sulfate, tween 80, tween 20, polyoxyl 40 stearate, polyoxyethylene 50 stearate, fusieates, bile salts, octoxynol and combinations thereof.

21. A method according to claim 13, wherein the surfactant is selected from the group of anionic, cationic and nonionic surfactants and combinations thereof.

* * * * *